(12) United States Patent
Inoue et al.

(10) Patent No.: US 9,116,136 B2
(45) Date of Patent: Aug. 25, 2015

(54) INSPECTION METHOD AND SYSTEM

(71) Applicant: NuFlare Technology, Inc, Numazu-shi, Shizuoka (JP)

(72) Inventors: Hiromu Inoue, Kanagawa (JP); Nobutaka Kikuiri, Tokyo (JP)

(73) Assignee: NUFLARE TECHNOLOGY, INC, Shizuoka (JP)

( * ) Notice: Subject to any disclaimer, the term of this patent is extended or adjusted under 35 U.S.C. 154(b) by 43 days.

(21) Appl. No.: 13/926,060

(22) Filed: Jun. 25, 2013

(65) Prior Publication Data
US 2014/0002826 A1    Jan. 2, 2014

(51) Int. Cl.
*G01B 11/24* (2006.01)
*G01N 21/956* (2006.01)
*G01N 21/95* (2006.01)

(52) U.S. Cl.
CPC .............. *G01N 21/956* (2013.01); *G01B 11/24* (2013.01); *G01N 21/9501* (2013.01); *G01N 21/95607* (2013.01); *G01N 21/9505* (2013.01)

(58) Field of Classification Search
CPC ....... G01B 11/24; G01N 21/956; G03H 1/26; G03G 21/00; G03B 27/42; G03B 27/32
USPC .................................. 356/399–401, 601–614
See application file for complete search history.

(56) References Cited

U.S. PATENT DOCUMENTS

| | | | |
|---|---|---|---|
| 6,995,828 B2* | 2/2006 | Okada | 355/30 |
| 7,164,464 B2* | 1/2007 | Okada | 355/53 |
| 2004/0070753 A1* | 4/2004 | Sugihara et al. | 356/237.5 |
| 2009/0207405 A1* | 8/2009 | Chikamatsu et al. | 356/237.2 |
| 2010/0214561 A1* | 8/2010 | Chikamatsu et al. | 356/237.5 |
| 2011/0255770 A1 | 10/2011 | Touya et al. | |
| 2014/0240700 A1 | 8/2014 | Ogawa et al. | |

FOREIGN PATENT DOCUMENTS

| | | |
|---|---|---|
| JP | 2003-294420 | 10/2003 |
| JP | 2007-248086 | 9/2007 |

(Continued)

OTHER PUBLICATIONS

Hiromu Inoue, et al., Inspection Apparatus and Inspection Method, U.S. Appl. No. 14/059,847, filed Oct. 22, 2013, not yet published, 50 pages.
Korean Office Action for Korean Patent Application No. 2013-0072942 mailed on Jun. 17, 2014.
(Continued)

*Primary Examiner* — Tarifur Chowdhury
*Assistant Examiner* — Isiaka Akanbi
(74) *Attorney, Agent, or Firm* — Amin, Turocy & Watson, LLP

(57) ABSTRACT

A sample, which has a mesa portion having a pattern thereon, is placed on a Z table. Light is irradiated to the mesa portion through an optical system and light reflected by the mesa portion is received to measure a height of the mesa portion. A height map of the mesa portion is created based on a height of a corner position. A height using the height map is corrected based on a deviation of a measured value from a target value, and a temporal variation of a focal position of light irradiated to the mesa portion. An optical image of the pattern is obtained based on the corrected height of the mesa portion. The optical image is compared with a reference image and a defect is determined when a difference value between the optical image and the reference image is more than a predetermined threshold value.

9 Claims, 15 Drawing Sheets

(56) References Cited

FOREIGN PATENT DOCUMENTS

| | | |
|---|---|---|
| JP | 2008-112178 | 5/2008 |
| JP | 2012-078164 | 4/2012 |
| KR | 2011-0113591 | 10/2011 |
| TW | 200644078 | 12/2006 |
| WO | 2009-149103 | 12/2009 |

OTHER PUBLICATIONS

Office Action of Notification of Examiner's Decision of Refusal for Taiwanese Patent Application No. 102120715 Dated Jan. 27, 2015, 8 pages.

Office Action for Taiwanese Patent Application No. 102120715 Dated Oct. 14, 2014, 13 pages.

* cited by examiner

INSPECTION METHOD AND SYSTEM

CROSS-REFERENCE TO THE RELATED APPLICATION

The entire disclosure of the Japanese Patent Application No. 2012-143975, filed on Jun. 27, 2013 including specification, claims, drawings, and summary, on which the Convention priority of the present application is based, are incorporated herein in its entirety.

FIELD OF THE INVENTION

This invention relates to an inspection method and an inspection apparatus and relates more specifically to an inspection method and an inspection apparatus for a sample with a mesa portion having a pattern thereon.

BACKGROUND

In a large scale integration (LSI), as the degree of integration and the capacity are increased, the circuit size required for a semiconductor device has been gradually narrowing. In the manufacture of the semiconductor device, a pattern is exposed and transferred onto a wafer by a reduced projection exposure apparatus generally called a stepper or scanner to form a circuit, using an original image pattern (meaning a mask or a reticle and hereinafter collectively referred to as a mask) formed with a circuit pattern, whereby the semiconductor device is manufactured.

Enhancement of yield is essential, as the manufacture of LSI requires a large manufacturing cost. Meanwhile, a recent typical logic device is under such a condition that the formation of a pattern with a line width of several ten nm is required. In these circumstances, a pattern defect of a mask and variation of process terms and conditions at the time of exposure and transfer constitute a major cause of reduction in the yield. Along with miniaturization of an LSI pattern dimension formed on a semiconductor wafer, the size of the pattern defect of a mask is also miniaturized. The dimensional accuracy of the mask is enhanced, whereby the fluctuation of the process terms and conditions is to be absorbed, and thus, in the inspection of a mask, an extremely small pattern is required to be detected. As a result, high inspection accuracy is required for an inspection apparatus, which detects a defect of a mask for transfer to be used in the manufacture of LSI.

In the inspection apparatus, light emitted from a light source is applied to a mask, which is to be inspected, through an optical system. The mask is placed on a table, and the irradiated light scans the mask by movement of the table. The light transmitted through or reflected by the mask is imaged on an image sensor through a lens, and an optical image imaged by the image sensor is sent as measurement data to a comparison part. In the comparison part, the measurement data and reference data are compared with each other in accordance with a suitable algorithm. When this data does not coincide with each other, it is determined that there is a defect (see, for example Japanese Patent Laid-Open Publication No. 2008-112178).

In response to the miniaturization of a pattern formed on a mask, realization of high magnification and high numerical aperture is advanced in an inspection optical system used for imaging an optical image of the pattern. Thus, a focus depth as an allowable range of a distance between an optical system and the mask becomes deeper, and a pattern image is blurred simply by slightly changing the distance between the optical system and the mask, so that a defect detection processing is hampered. Because of this, an automatic focus mechanism is used to fix the distance between the optical system and the mask at all times.

Japanese Patent Laid-Open Publication No. 2003-294420 discloses an automatic focus mechanism which a focal position of an inspection optical system is aligned with a surface of a mask. In this automatic focus mechanism, when the mask is irradiated with light from a light source, the light reflected by the mask enters an optical sensor. Subsequently, an electrical signal of the incident light is converted into a digital signal and then input into a height measuring circuit. In the height measuring circuit, a differential signal with respect to an input offset value and a target height are output. The differential signal is input to a Z table driving circuit used for driving a Z table. Then, the Z table drive circuit drives the Z table in accordance with the differential signal. Consequently, the distance between the optical system and the mask can be fixed.

Recently, as a technique for forming a fine pattern, nanoimprint lithography (NIL) has attracted attention. In this technique, a mold (die) having a nanoscale microstructure is pressure applied to a resist on a wafer to form the fine pattern on the resist.

In the nanoimprint technology, to increase productivity, duplicate templates (replica templates) are produced using a master template as an original plate, and the replica templates are mounted and used in different nanoimprint apparatuses. The replica template is required to be produced so as to accurately correspond to the master template. Thus, high inspection accuracy is required when the replica template is inspected.

The replica template has a mesa structure in which the central portion protrudes relative to the outer circumferential portion, and a pattern is formed on the protruding portion (referred to as a mesa portion or a land portion). According to this structure, when the pattern is transferred onto a resist, the occurrence of unnecessary contact between the replica template and the resist can be prevented.

When a pattern defect of the replica template is inspected, a surface of the replica template is scanned with light from a light source. At this time, since there is a step between the mesa portion and the other portions, there is a problem that tracking of a focus control using an automatic focus mechanism cannot be performed. For example, the light is applied to the step or an end of the mesa portion, and when the light diffused by the step or the end of the mesa portion is reflected to enter a height measuring circuit, the light may focus on a position which is not a focal position. Alternatively, when the light passes through the step, although the height of a table is significantly reduced to incorporate the portion into an imaging surface, if the control using a Z table driving circuit cannot be tracked at this time, the distance between the optical system and a surface to be inspected is no longer fixed, so that a pattern image is blurred.

The present invention has been made in consideration of the above points, and provides an inspection method and an inspection apparatus in which a sample having a mesa portion with a pattern can be accurately inspected.

Other challenges and advantages of the present invention are apparent from the following description.

SUMMARY OF THE INVENTION

According to one aspect of the present invention, an inspection method comprising, placing a sample, which has a mesa portion having a pattern thereon, on a table, irradiating light to the mesa portion through an optical system, and receiving light reflected by the mesa portion for measuring a height of the mesa portion, creating a height map of the mesa portion based on a height of a corner position of the mesa portion, correcting a height of the mesa portion using the height map based on a deviation of a measured value of the height of the mesa portion from a target value, and a temporal variation of a focal position of light irradiated to the mesa portion, obtaining an optical image of the pattern while controlling a position of the table based on the corrected height of the mesa portion, and comparing the optical image with a reference image and determining a defect when a difference value between the optical image and the reference image is more than a predetermined threshold value.

Further to this aspect of the present invention an inspection method, wherein the height of the mesa portion is measured while the optical image of the pattern is obtained, and a temporal variation of the focal position of light is obtained based on the height of the measured mesa portion.

Further to this aspect of the present invention an inspection method, wherein a temporal variation of the focal position of light is obtained from a change of atmospheric pressure.

According to another aspect of the present invention, an inspection method comprising, placing a sample, which has a mesa portion having a pattern thereon, on a table, irradiating light to the mesa portion through an optical system, and receiving light reflected by the mesa portion for measuring a height of the mesa portion to obtain an inclination amount of a surface having the pattern relative to a horizontal surface of a sample, creating a height map of the mesa portion from the height of the corner positions of the mesa portion, correcting a height of the mesa portion using the height map based on a deviation of a measured value of the height of the mesa portion from a target value, and a temporal variation of a focal position of light irradiated to the mesa portion, obtaining an optical image of the pattern while controlling a position of the table based on the corrected height of the mesa portion, and comparing the optical image with a reference image and determining a defect when a difference value between the optical image and the reference image is more than a predetermined threshold value, wherein in the step of obtaining the optical image, when a measured value of the height of the mesa portion at one position is at a predetermined value or is more than a predetermined value, the measured value is corrected, the position of the table is adjusted based on the corrected measured value, and then the height of the mesa portion in the next frame is measured.

Further to this aspect of the present invention, an inspection method, wherein the sample is supported at three points by supporting parts provided on the table, and in the step of inclining the sample, heights of the supporting parts at the three points are adjusted.

According to another aspect of the present invention, an inspection method comprising, placing a sample, which has a mesa portion having a pattern thereon, on a table, irradiating light to the mesa portion through an optical system, and receiving light reflected by the mesa portion for measuring a height of the mesa portion, creating a height map of the mesa portion based on a height of a corner position of the mesa portion, correcting the height of the mesa portion using the height map based on a deviation of a measured value of the height of the mesa portion from a target value, and a variation according to atmospheric pressure at the focal position of light irradiated to the mesa portion, obtaining an optical image of the pattern while controlling a position of the table based on the corrected height of the mesa portion, and comparing the optical image with a reference image and determining a defect when a difference value between the optical image and the reference image is more than a predetermined threshold value.

According to another aspect of the present invention, an inspection apparatus comprising, a table on which a sample is placed, a light source which applies light toward the sample placed on the table, a height measuring portion which receives the light from the light source reflected by the sample and creates height data of a surface of the sample, a signal generating portion which generates different signals according to whether the sample has a mesa portion, a signal switching portion which switches a destination to which the height data is transmitted according to a signal from the signal generation portion, a map creating portion which receives the height data and creates a height map of the mesa portion based on a height of a corner positions of the mesa portion of the sample, a height correcting portion which corrects the height of the mesa portion using the height map based on a deviation of a measured value of the height of the mesa portion from a target value, and a temporal variation of a focal position of light irradiated to the mesa portion, a height control portion which receives the height data, or the corrected height data of the mesa portion corrected by the height correcting portion and controls a position of the table, an optical image acquisition portion which obtains an optical image of the sample, and a comparison portion which compares the optical image with a reference image and determines a defect when a difference value between the optical image and the reference image is more than a predetermined threshold value.

Further to this aspect of the present invention, an inspection apparatus, further comprising, a barometer which measures atmospheric pressure, wherein the height correcting portion receives the height data from the height measuring portion, the height map from the map creating portion, and the atmospheric pressure data measured by the barometer, a difference between the height data from the height measuring portion and height data as a target value is a deviation from a target value of the measured value of the height of the mesa portion, a variation of a height according to the atmospheric pressure obtained from the atmospheric pressure data is used as a temporal variation of the focal position of light irradiated to the mesa portion, and the height of the mesa portion obtained from the height map is corrected.

Further to this aspect of the present invention, an inspection apparatus, wherein the sample is supported at three points by supporting parts provided on the table, and in the step of inclining the sample, heights of the supporting parts at the three points are adjusted.

DETAILED DESCRIPTION OF THE EMBODIMENTS

Embodiment 1

Figure 1:
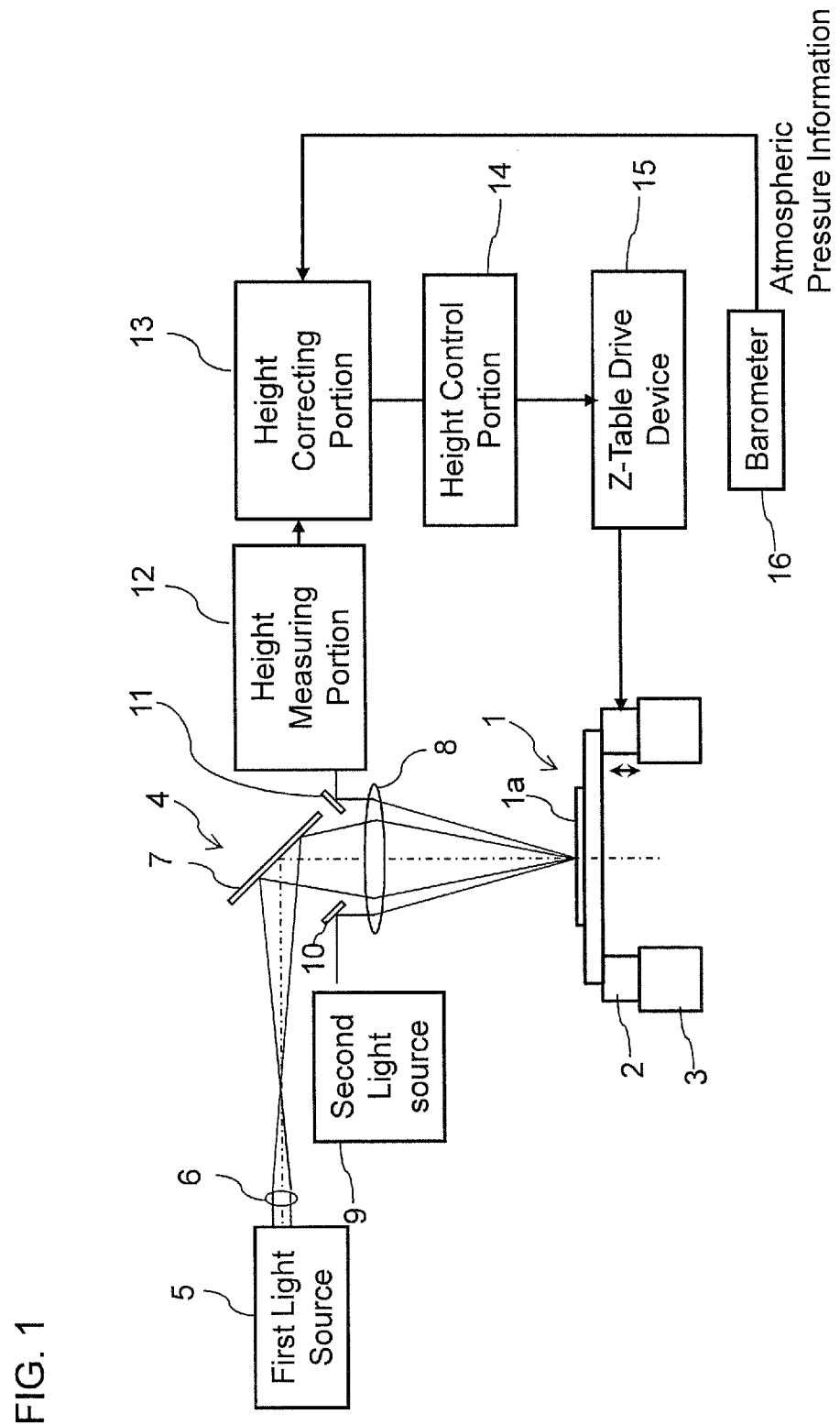
FIG. 1 is a diagram illustrating the configuration of an automatic focus mechanism according to embodiment 1.

FIG. 1 is a diagram illustrating the configuration of an automatic focus mechanism according to embodiment 1.

In FIG. 1, a sample 1 is mounted on a Z table 2 provided to be movable in vertical direction. The table 2 is movable in horizontal direction by a XY table 3. The sample 1 has a mesa structure in which the central portion protrudes relative to the outer circumferential portion, and a pattern to be inspected is formed on a rectangular mesa portion (referred to as a land portion) 1a. As the sample 1, a replica template used in the nanoimprint technology is used, for example.

An optical system 4 is disposed above the sample 1. In the optical system 4, a first light source 5 applies light for defect inspection to the sample 1. The light emitted from the first light source 5 is transmitted through a lens 6 and the direction of light is changed by a mirror 7, and, thus, is focused on the sample 1 by a lens 8. A photodiode array (not illustrated) is disposed under the sample 1, and light transmitted through the sample 1 is imaged on the photodiode array, so that an optical image (to be described later) is generated.

An inspection region on the sample 1 is virtually divided into a plurality of strip-shaped inspection frames, and the operation of an XY table 3 of FIG. 1 is controlled so that the respective divided inspection frames are continuously scanned.

In the optical system 4, a second light source 9 applies light for height measurement to the sample 1. The mirror 10 changes the direction of the light emitted from the second light source 9, and the light is irradiated onto the sample 1. Subsequently, the light is reflected from the sample 1 and then enters a height measuring portion 12 via the mirror 11. In the optical system 4 of FIG. 1, a light projecting lens through which the light emitted from the second light source 9 is focused on the sample 1 and a light receiving lens which receives the light reflected from the sample 1 and converges the light are omitted.

The height measuring portion 12 has a light-receiving element (not illustrated). As the light-receiving element, a position sensitive detector (PSD) is used, as one example. The PSD has a similar structure to a PIN type photodiode, and in the PSD, a photocurrent is measured using a photovoltaic effect to realize measurement of the center of gravity of light.

In the height measuring portion 12, a signal output from the light-receiving element is converted from a current value to a voltage value by an I/V conversion amplifier. After that, the signal is amplified to a suitable voltage level by a noninverting amplification amplifier and then converted into digital data in an A/D converting portion, and the height data of the surface of the sample 1 corresponding to a position of light detected by the light-receiving element is created.

A specific example of a method for creating the height data is as follows.

The light emitted from the second light source 9 is converged on the surface of the sample 1 by the projecting lens. The converged light is reflected by the surface of the sample 1 to enter the light-receiving lens, and, thus, to be converged on the PSD. When spot light enters the PSD, an electric charge proportional to light energy is generated at the incident position, and a current passes through a resistive layer (P layer) having a uniform resistance value, and, thus, flows to an electrode installed at two end surfaces on the PSD. The amount of current at this time is divided inversely proportional to a distance to the electrode. When a current output from the electrode installed at one end surface is represented by $I_1$, and a current output from the electrode installed at the other end surface is represented by $I_2$, the center-of-gravity X from the center of the PSD in the spot light can be obtained from the following formula (1). In the formula (1), L is a length of a light-receiving surface. An all-optical current showing a light-receiving intensity of the PSD is obtained from the sum of $I_1$ and $I_2$.

$$X = L/2 \times (I_1 - I_2)/(I_1 - I_2) \tag{1}$$

The center of gravity of the incident light is obtained by measuring two current variations. Thus, an I/V conversion circuit is typically constituted, output current changes ($I_1$, $I_2$) from the PSD are individually converted into output voltage changes ($V_1$, $V_2$), and the center of gravity of light is measured. At this time, since a dark current of the light-receiving element, a leakage current on a circuit, and an offset current of the I/V conversion amplifier exist as manufacturing errors, the sum of the amounts of these currents that is an offset voltage ($V_{10}$, $V_{20}$) of the entire circuit acts upon the output voltage. Namely, when the output voltages after voltage conversion are represented by $V_1$, $V_2$, a height Z to be measured is represented by the following formula (2). In the formula (2), α is a coefficient determined from the measurement range of a sample height and a center-of-gravity moving range of light on the PSD.

$$Z = \alpha \times (V_1 - V_2)/(V_1 + V_2) \tag{2}$$

However, considering the offset voltage, a height Z' to be measured actually is represented by the following formula (3). In the formula (3), $V_{10}$, $V_{20}$ each are offset voltages.

$$Z' = \alpha \times \{(V_1 + V_{10}) - (V_2 + V_{20})\}/\{(V_1 + V_{10}) + (V_2 + V_{20})\} \tag{3}$$

In the sample 1, since there is a step between a mesa portion 1a and the other portions, tracking of a focus control using an automatic focus mechanism cannot be performed. Thus, in this embodiment, an inclination amount of a pattern surface of the mesa portion 1a relative to a horizontal surface of the sample and, more specifically, a scanning surface of light irradiated to the sample 1 is obtained from height data at a corner position (for example, four corners) of the mesa portion 1a.

Figure 2:
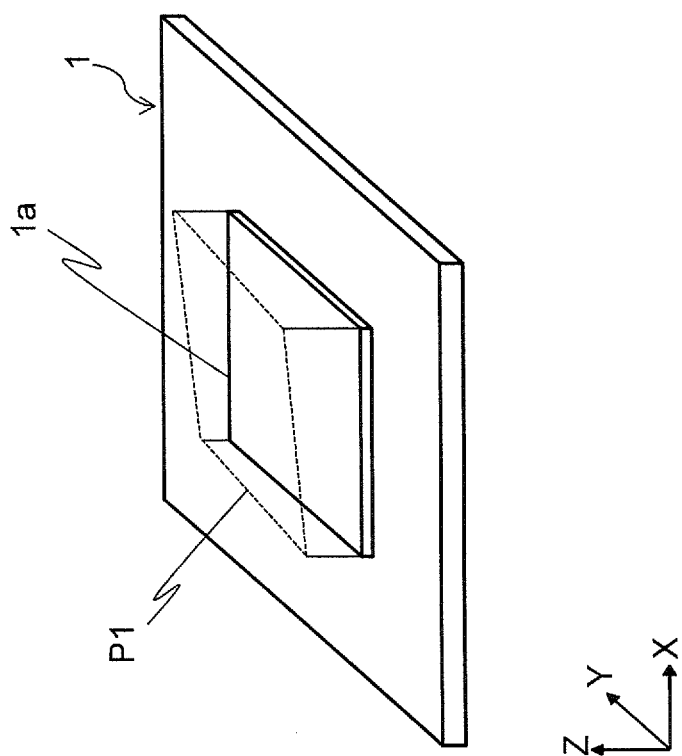
FIG. 2 illustrates a state in which a pattern surface of the mesa portion is inclined in one direction relative to the horizontal surface in the embodiment 1.

FIG. 2 illustrates a state in which a pattern surface P1 of the mesa portion 1a is inclined in one direction relative to the horizontal surface. More specifically, a Z position in a +X direction is higher than the Z position in a −X direction relative to a Y position. Thus, a sample surface is inclined in the arrow direction in FIG. 3 so that the pattern surface P1 is horizontal. According to this constitution, a distance between the optical system 4 and the sample 1 is fixed, and a focus displacement amount can be also fixed.

Figure 3:
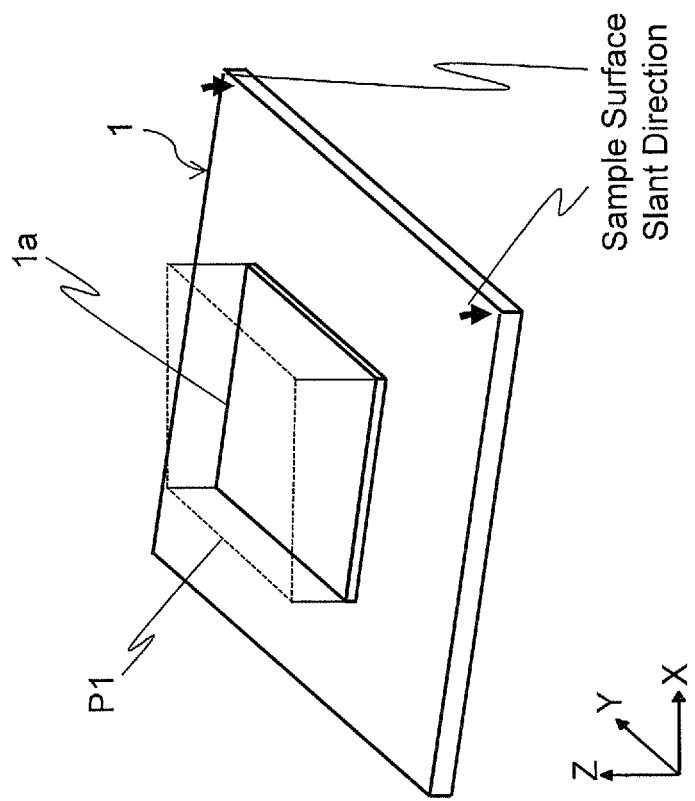
FIG. 3 illustrates a state in which a sample surface is inclined so that the pattern surface of FIG. 2 is horizontal.

In FIG. 1, a height correcting portion 13 obtains the inclination amount of the pattern surface relative to the horizontal surface based on the height data from the height measuring portion 12. A height control portion 14 controls a Z table drive device 15 based on the inclination amount from the height correcting portion 13 and inclines the sample 1 so that the inclination amount of the mesa portion 1a is zero. Consequently, as illustrated in FIG. 3, the pattern surface P1 coincides with the horizontal surface, and the distance between the optical system 4 and the sample 1 can be fixed.

Figure 15:
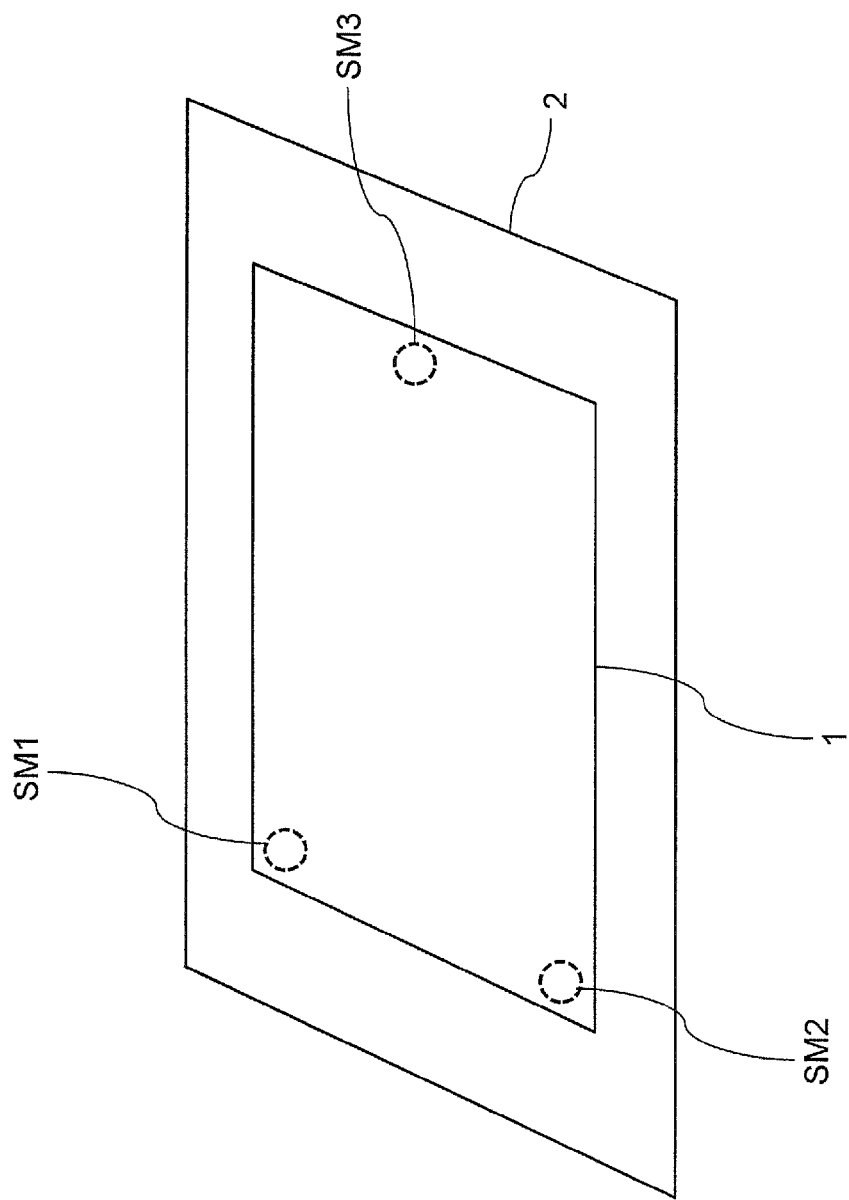
FIG. 15 illustrates a state in which the supporting parts support a sample at three points.

In this embodiment, it is preferable that the sample 1 is supported at three points by supporting parts provided on the Z table 2. When the sample 1 is supported at four points, the height of the supporting part is required to be adjusted with higher accuracy. If the height adjustment is insufficient, the sample 1 may be deformed. On the contrary, according to the three-point support, the sample 1 can be supported while the deformation of the sample 1 is suppressed to a minimum. The supporting part is constituted using a ball point having a spherical head surface. As shown in FIG. 15, two (SM1, SM2) of the three supporting parts (SM1, SM2, SM3) are in contact with the sample 1 at the adjacent two corners which are not opposing corners of four corners of the sample 1. The remaining one supporting part (SM3) is disposed in a region between the two corners where the other two supporting parts (SM1, SM2) are not arranged. Each height of the supporting parts (SM1, SM2, SM3) is adjusted, whereby the sample 1 can be inclined so that the pattern surface P1 coincides with the horizontal surface.

When the atmospheric pressure and temperature change in the inspection process, the focal position of light irradiated to the mesa portion 1a is changed, and the height data of the corner positions of the mesa portion 1a fluctuates.

For example, when the atmospheric pressure changes, the refractive index of air changes, whereby an imaging surface of an object, that is, the focal position is changed, and focus displacement occurs. Thus, even if the inclination of the sample surface is changed to fix a focus displacement amount using the above method, the focus displacement amount fluctuates as a result of the change of the atmospheric pressure. Thus, the variation of the atmospheric pressure is measured, a temporal focus displacement amount is obtained from the value, and the height of the mesa portion 1a is corrected.

Figure 4:
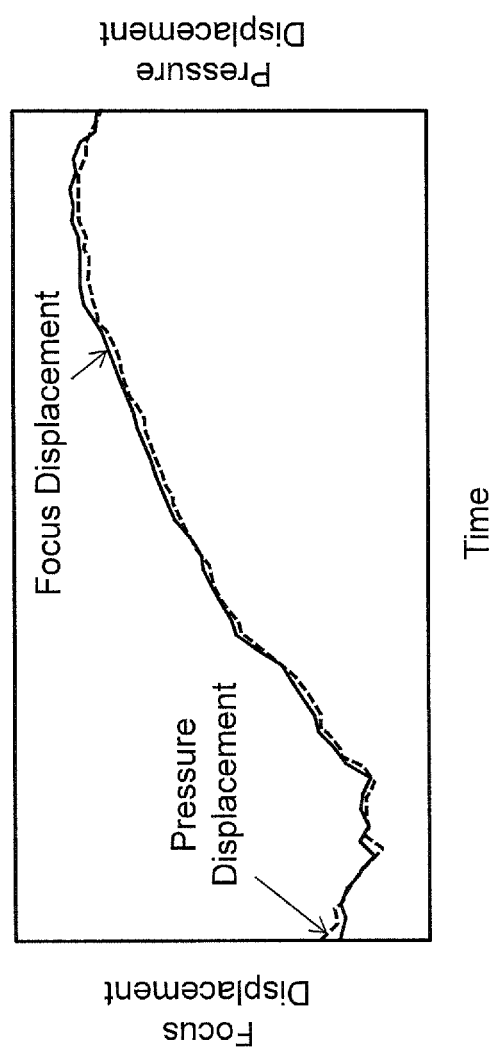
FIG. 4 illustrates an example showing each temporal change of the atmospheric pressure and a focus displacement.

FIG. 4 illustrates an example showing each temporal change of the atmospheric pressure and the focus displacement. As seen in FIG. 4, a change of the atmospheric pressure and a change of the focus displacement are correlated with each other. Accordingly, the focus displacement amount can be predicted by measuring the atmospheric pressure change. Thus, as illustrated in FIG. 1, the measurement result from the barometer 16 as atmospheric pressure information is sent to the height correcting portion 13. The height correcting portion 13 obtains the focus displacement amount based on the atmospheric pressure information sent from the barometer 16. Subsequently, the height data from the height measuring portion 12 is corrected using the focus displacement amount.

The height control portion 14 receives the corrected height data from the height correcting portion 13. The height control portion 14 then controls the Z table drive device 15 based on the height data so that the height of the mesa portion 1a is a target value. The target value may be regarded as the height where the focal position of light irradiated to the mesa portion 1a coincides with the pattern surface.

In this embodiment, the height data based on atmospheric pressure and temperature can be corrected as follows.

For example, when light for defect inspection is scanned on the mesa portion 1a, the height data of the mesa portion 1a is created in the height measuring portion 12. At this time, the variation of the height data is obtained for each inspection frame. When the height variation of the mesa portion 1a in a single inspection frame is not less than a predetermined value, the height data is corrected in the height correcting portion 13. The Z table drive device 15 adjusts the position of the Z table 2 based on the corrected height data so that the height of the mesa portion 1a is a target value. Then, the next inspection frame is scanned. An effective area available for the height measurement is set inside the mesa portion 1a to be separated at a predetermined distance from a step portion.

Figure 5:
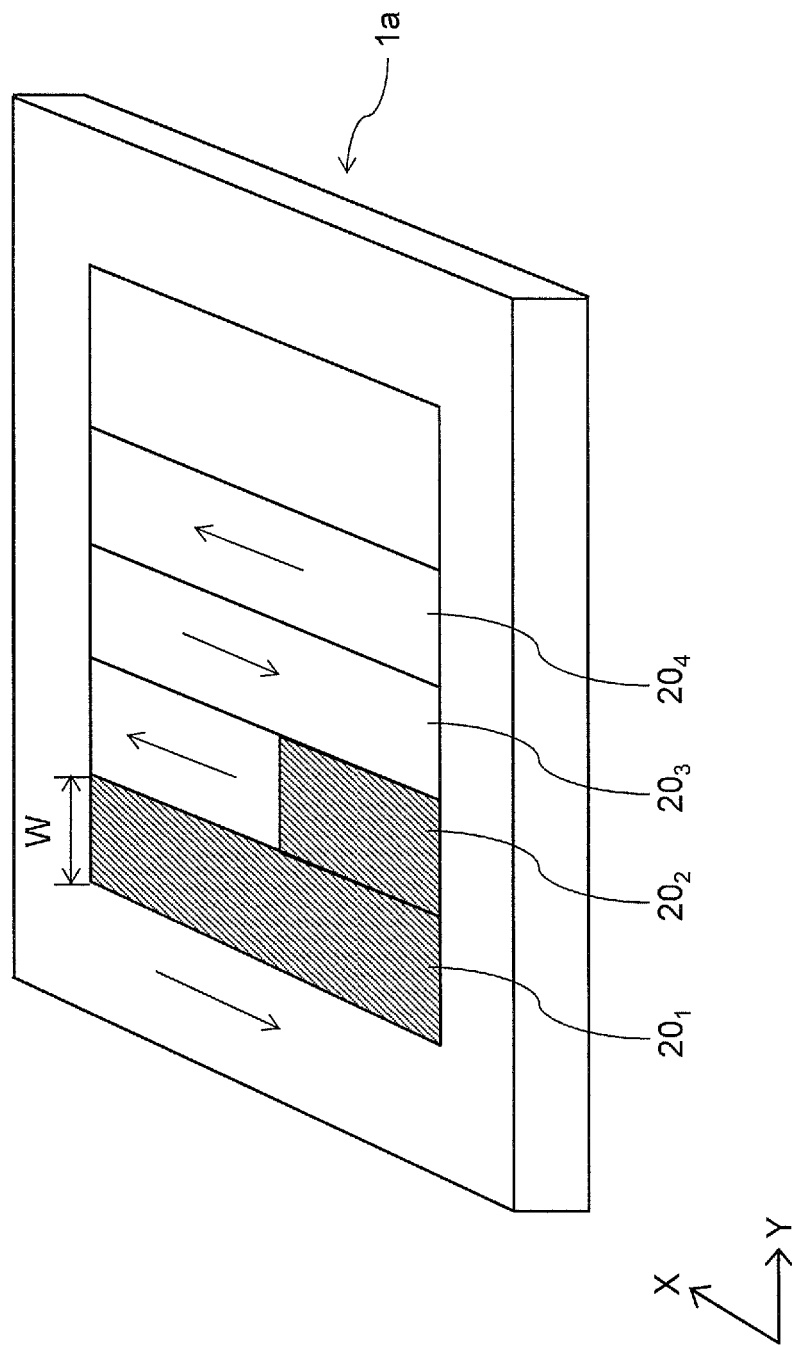
FIG. 5 is a diagram illustrating the way in which an optical image used for inspecting the defects is acquired.

FIG. 5 is a diagram illustrating the way in which an optical image used for inspecting the defects is acquired.

As illustrated in FIG. 5, the inspection region of the mesa portion 1a is virtually divided into the strip-shaped inspection frames with a scan width W in the Y direction, and the operation of the XY table 3 of FIG. 1 is controlled so that the respective divided inspection frames $20_1$, $20_2$, $20_3$, $20_4$, etc. are continuously scanned, and an optical image is obtained while the XY table 3 moves in the X direction. Then, images with the scan width W illustrated in FIG. 5 are continuously input to the photodiode array. After an image in the first inspection frame $20_1$ is obtained, images with the scan width W are similarly continuously input while an image in the second inspection frame $20_2$ is moved in the opposite direction this time. When the image in the third inspection frame $20_3$ is obtained, the XY table 3 moves in a direction opposite to the direction in which the image in the second inspection frame $20_2$ is obtained, that is, in the direction in which the image in the first inspection frame $20_1$ has been obtained. The diagonal portion of FIG. 5 schematically represents a region in which an optical image has been obtained as described above.

In this embodiment, in the inspection frames $20_1$, $20_2$, $20_3$, $20_4$, etc., the height of the mesa portion 1a is measured while obtaining an optical image of a pattern, and the displacement amount of the height data is obtained in each inspection frame. Then, for example, when the height variation of the mesa portion 1a in a single inspection frame $20_1$ is not less than a predetermined value, the height data is corrected in the height correcting portion 13. The Z table drive device 15 adjusts the position of the Z table 2 based on the corrected height data so that the height of the mesa portion 1a is a target value. Then, the next inspection frame $20_2$ is scanned.

Further, in this embodiment, the height of the mesa portion 1a can be measured at the start of each inspection As described above, according to this embodiment, the sample surface is inclined so that the focus displacement amount is constant in the pattern surface, whereby the distance between the optical system 4 and the sample 1 is fixed.

A temporal variation of the focal position of light irradiated to the mesa portion 1a, that is, a temporal focus displacement amount is obtained, and an optical image of a pattern is obtained while the position of the Z table 2 is controlled based on the value of the temporal focus displacement amount. According to this method, the sample 1 can be accurately inspected. When the temporal variation of the focal position is obtained from the atmospheric pressure change, an influence of an atmospheric pressure variation on the inspection can be reduced.

Alternatively, when an optical image of a pattern is obtained, the height data of the mesa portion 1a is created by the height measuring portion 12, and when a measured value of the height of the mesa portion 1a in a single frame fluctuates at a predetermined value, or more than a predetermined value, the measured value is corrected. The position of the Z table 2 is adjusted based on an obtained correction value, and then the height of the mesa portion 1a in the next frame is measured. According to this method, even if the focal position of the light irradiated to the mesa portion 1a fluctuates as a result of a temperature change in the inspection process, the sample 1 can be accurately inspected.

Figure 6:
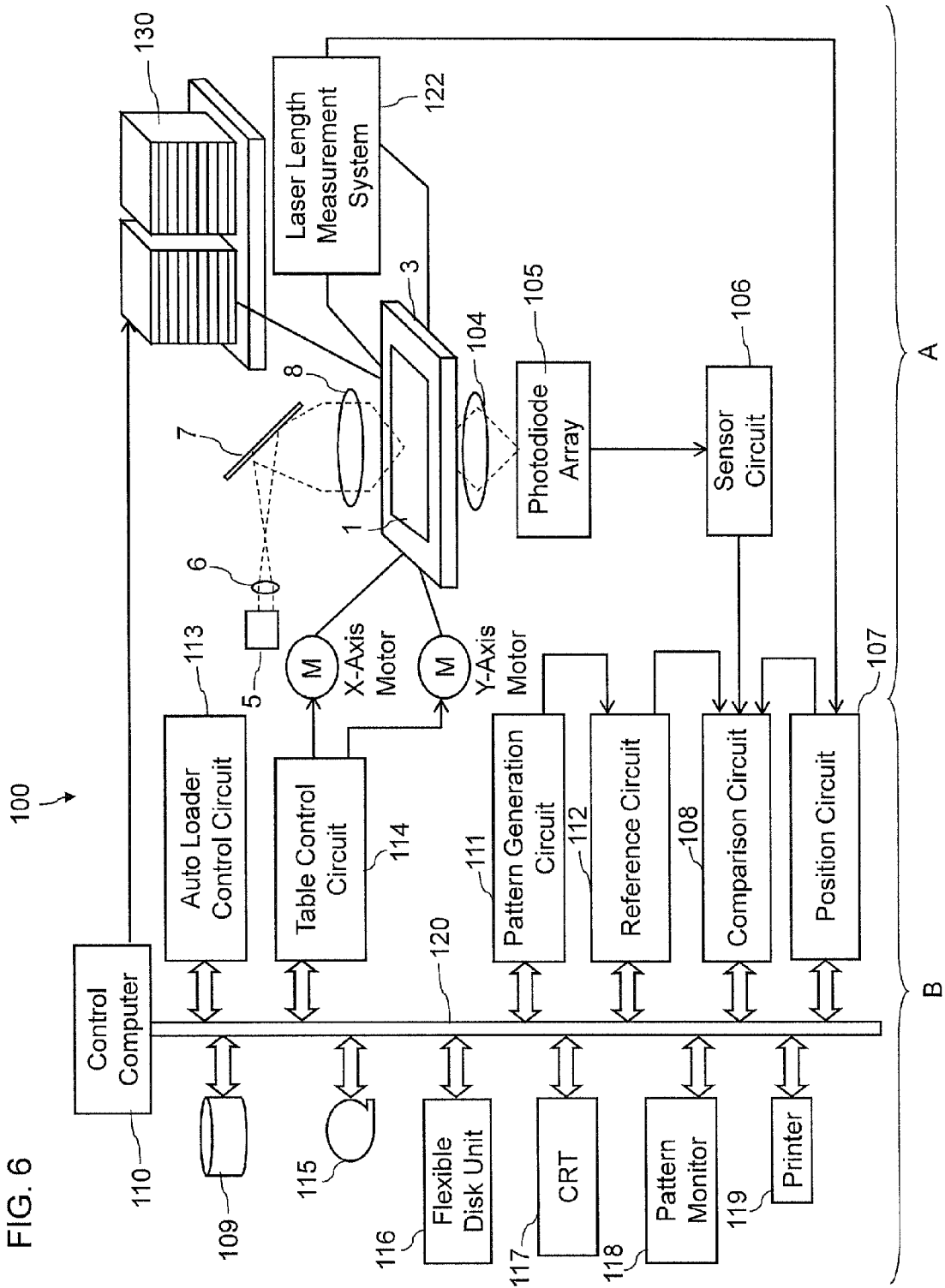
FIG. 6 is a diagram showing the configuration of an inspection system according to the embodiment 1.

FIG. 6 is a diagram showing the configuration of an inspection system 100 according to the present embodiment. Although the inspection apparatus 100 includes the automatic focus mechanism of FIG. 1, an optical system for defect inspection and components other than an XY table 3 are omitted.

As illustrated in FIG. 6, the inspection apparatus 100 has an optical image acquisition unit A and a control unit B.

The optical image acquisition unit A has the first light source 5, the XY table 3 movable in the horizontal direction (X and Y directions), the lenses 6 and 8, a lens 104, the mirror 7, a photodiode array 105, a sensor circuit 106, a laser length measurement system 122, and an autoloader 130. The XY table 3 has a structure capable of moving in a rotational direction (θ direction).

In the control unit B, a control calculator 110 responsible for the overall control of the inspection apparatus 100 is connected to a position circuit 107, a comparison circuit 108, a reference circuit 112, a pattern generation circuit 111, an autoloader control circuit 113, a table control circuit 114, a magnetic disk device 109 as an example of a storage device, a magnetic tape device 115, a flexible disk device 116, a CRT (Cathode Ray Tube) 117, a pattern monitor 118, and a printer 119 via a bus 120 as a data transmission path. The XY table 3 is driven by an X-axis motor and a Y-axis motor controlled by the table control circuit 114. As those motors, a step motor may be used, for example.

Design pattern data which is database reference data is stored in the magnetic disk device 109 and read out in accordance with progression of the inspection to be sent to the pattern generation circuit 111. In the pattern generation circuit 111, the design pattern data is converted into image data (design pixel data). After that, the image data is sent to the reference circuit 112 and used in the generation of a reference image.

The inspection apparatus of this embodiment may include other well-known components required for the inspection of the sample 1 in addition to the constituent elements illustrated in FIG. 6. For example, the inspection apparatus itself may have a review device (to be described later).

Figure 7:
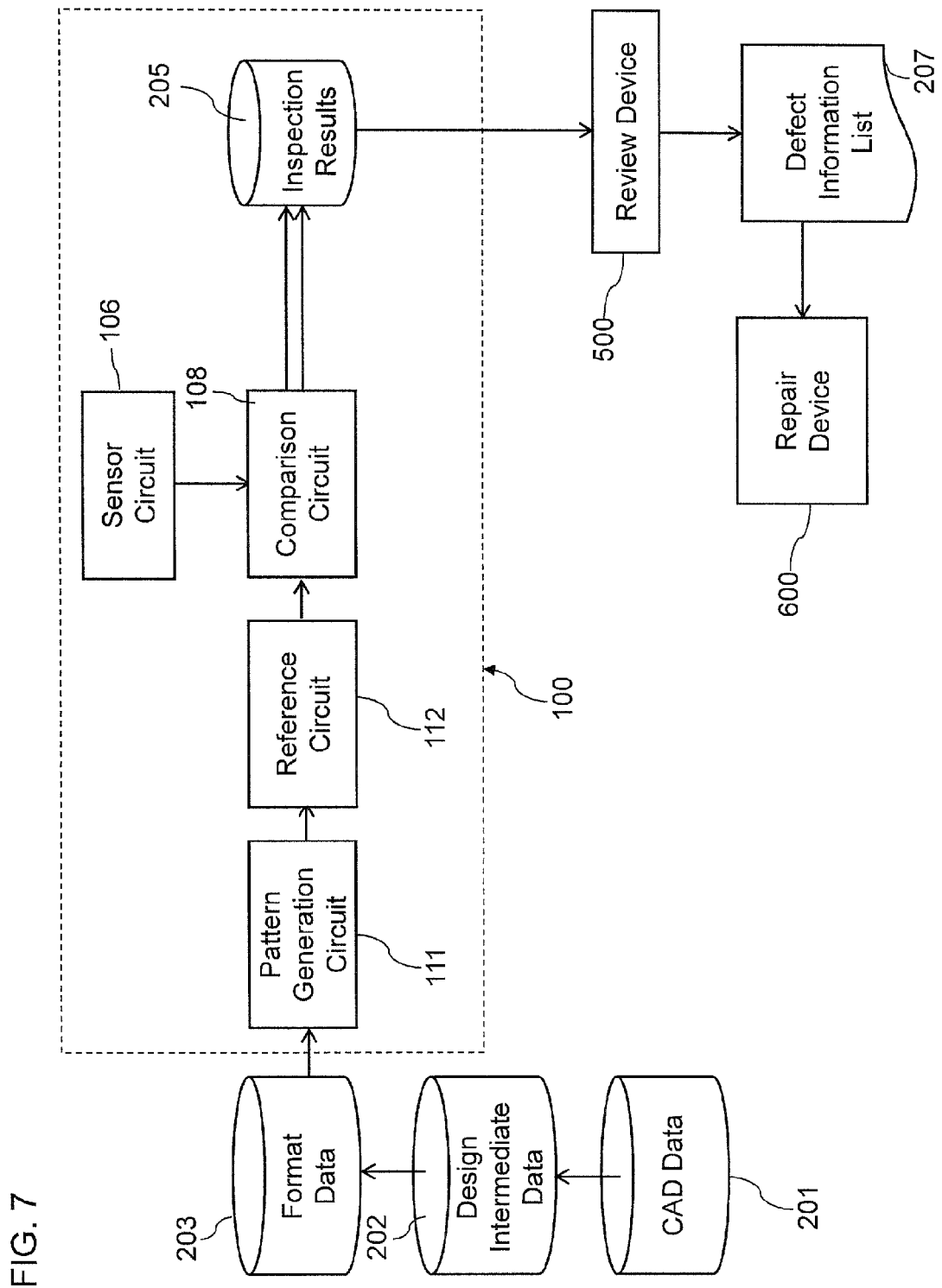
FIG. 7 is a schematic diagram showing a flow of data in the inspection apparatus of FIG. 6.

FIG. 7 is a schematic diagram showing a flow of data in this embodiment.

As illustrated in FIG. 7, CAD data 201 created by a designer (user) is converted into design intermediate data 202 having a hierarchized format. The design intermediate data 202 stores pattern data created for each layer and formed in the sample 1. In general, the inspection apparatus is not configured to be capable of directly reading the design intermediate data 202. Namely, different format data is used for each manufacturer of an inspection apparatus. Thus, the design intermediate data 202 is converted into format data 203, inherent in each inspection apparatus, for each layer and then input to the inspection apparatus 100. In this case, the format data 203 can be used as data inherent in the inspection apparatus 100.

Figure 8:
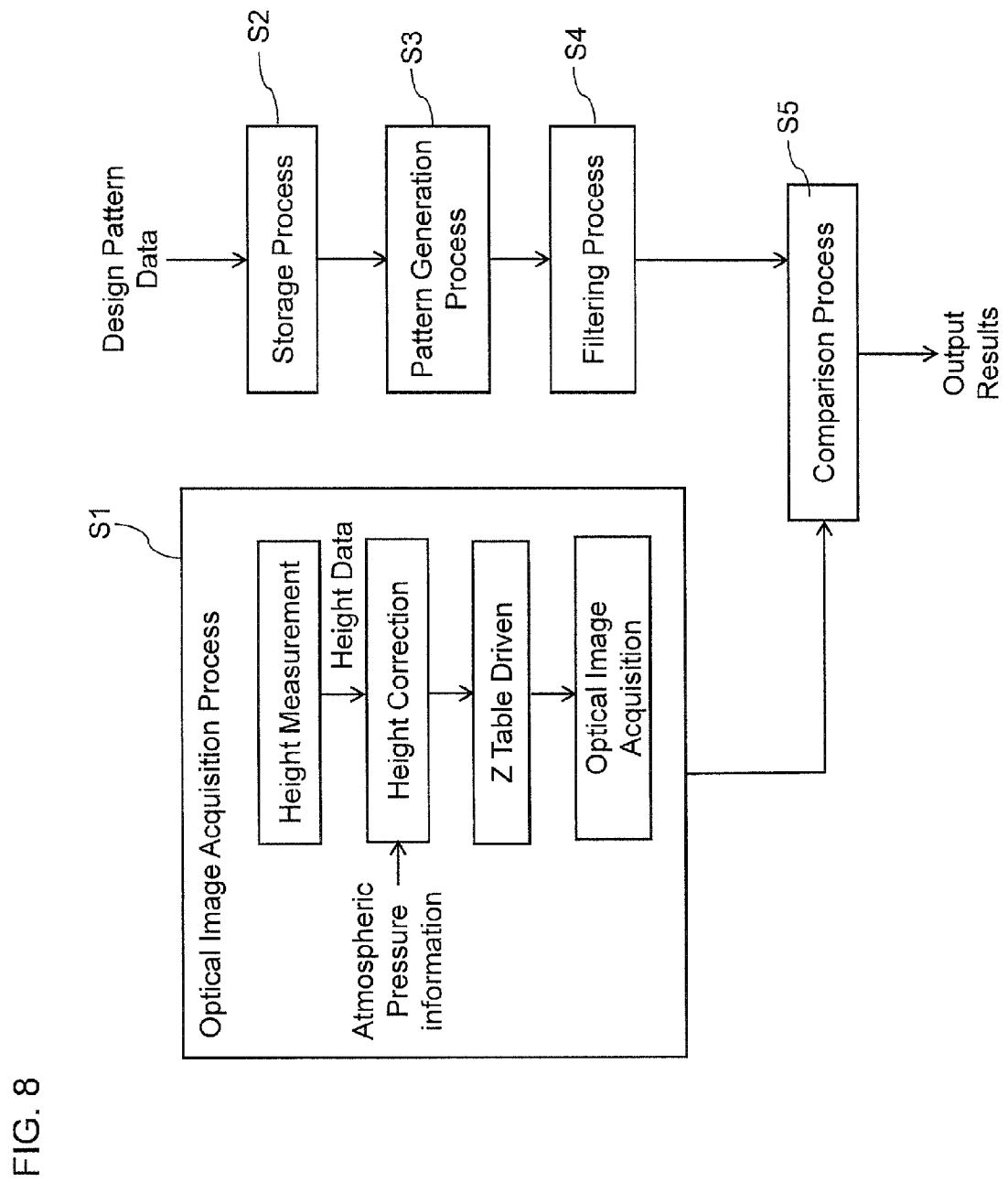
FIG. 8 is a flowchart showing an inspection process according to the embodiment 1.

FIG. 8 is a flowchart showing an inspection process. Hereinafter, an inspection method according to a die-to-database method will be described. Accordingly, a reference image compared with an optical image to be inspected is a reference image created based on drawing data (design pattern data). However, the inspection apparatus of this invention can be applied to the inspection method according to the die-to-database method, and a reference image in this case is an optical image different from the optical image to be inspected.

As illustrated in FIG. 8, the inspection process has an optical image acquisition process (S1), a storage process (S2) for the design pattern data, a pattern generation process (S3) and a filtering process (S4) as examples of a reference image generation process, and a comparison process (S5) for an optical image and a reference image.

<Optical Image Acquisition Process>

In FIG. 8, in the optical image acquisition process S1, the optical image acquisition unit A of FIG. 6 obtains the optical image (measurement data) of the sample 1. The optical image is an image of the sample 1 on which a graphic based on graphic data included in design pattern is drawn. A specific example of a method of obtaining the optical image will be described using FIGS. 1 and 6.

The sample 1 is placed on the Z table 2. The Z table 2 can be moved in a horizontal direction by the XY table 3. More specifically, the XY table 3 is driven by the table control circuit 114 under the control of the control calculator 110 of FIG. 6 and can be moved by a drive system which drives the XY table 3 in the X and Y directions. As the X-axis and Y-axis motors, a step motor may be used, for example. The position of the movement of the XY table 3 is measured by the laser length measurement system 122 and sent to the position circuit 107. The sample 1 on the XY table 3 is automatically conveyed from the autoloader 130 driven by the autoloader control circuit 113, and the sample 1 is automatically discharged after the termination of the inspection.

The first light source 5 applies light for defect inspection to the sample 1. The light emitted from the first light source 5 is transmitted through the lens 6 and the direction is changed via the mirror 7, and, thus, is focused on the sample 1 by the lens 8.

A distance between the lens 8 and the sample 1 is kept constant as follows.

In FIG. 1, the second light source 9 applies light for height measurement to the sample 1. The mirror 10 changes the direction of the light emitted from the second light source 9, and the light is irradiated onto the sample 1. Subsequently, the light is reflected from the sample 1 and then enters the height measuring portion 12 via the mirror 11.

In the height measuring portion 12, the height data of the surface of the sample 1 is created. Subsequently, in the height correcting portion 13, the inclination amount of the pattern surface of the mesa portion 1a relative to the horizontal surface and, more specifically, the scanning surface of light irradiated to the sample 1 is obtained based on the height data from the height measuring portion 12. Next, the height control portion 14 controls a Z table drive device 15 based on the inclination amount from the height correcting portion 13.

Specifically, the height correcting portion 13 obtains the inclination amount of the pattern surface relative to the horizontal surface based on the height data from the height measuring portion 12. The height control portion 14 controls the Z table drive device 15 based on the inclination amount from the height correcting portion 13 and inclines the sample 1 so that the inclination amount of the mesa portion 1a is zero. Consequently, as illustrated in FIG. 3, the pattern surface P1 coincides with the horizontal surface, and the distance between the optical system 4 and the sample 1 can be fixed. During the inspection, for example, the measurement result from the barometer 16 as atmospheric pressure information is sent to the height correcting portion 13. The height correcting portion obtains the focus displacement amount based on the atmospheric pressure information sent from the barometer 16. Subsequently, the height data from the height measuring portion 12 is corrected using the focus displacement amount. The height control portion 14 receives the corrected height data from the height correcting portion 13. The height control portion 14 then controls the Z table drive device 15 based on the height data so that the height of the mesa portion 1a is a target value. Thereby, the focus displacement amount can be fixed.

As illustrated in FIG. 6, light irradiated from the first light source 5 and transmitted through the sample 1 is imaged as an optical image on the photodiode array 105 through the lens 104.

A procedure of obtaining the optical image in the inspection region of the sample 1 is as described above using FIG. 5. An image of a pattern imaged on the photodiode array 105 of FIG. 6 is photoelectrically converted by the photodiode array 105 and further A/D (analogue/digital) converted by the sensor circuit 106. An image sensor is disposed on the photodiode array 105. As the image sensor of this embodiment, a line sensor in which CCD cameras as imaging devices are arranged in a row is used, for example. The line sensor includes a TDI (Time Delay Integration) sensor. A pattern of the sample 1 is imaged by the TDI sensor while the XY table 3 continuously moves in the X-axis direction.

A distance between the lens 8 and the sample 1 is changed by atmospheric pressure and temperature. Accordingly, the focus displacement amount created based on the height data is required to be corrected in response to variations of the atmospheric pressure and temperature. For example, the atmospheric pressure information measured by the barometer 16 of FIG. 1 is sent to the height correcting portion 13, and the height data from the height measuring portion 12 is corrected based on the atmospheric pressure information. The height control portion 14 receives the corrected focus displacement amount from the height correcting portion 13. The Z table drive device 15 is then controlled based on the focus displacement amount. Consequently, the pattern surface of the sample 1 coincides with the horizontal surface, so that the focus displacement amount can be always fixed.

The optical image thus obtained in the optical image acquisition process (S1) is sent to the comparison circuit 108 of FIG. 6.

<Storage Process>

In FIG. 8, S2 is the storage process. In FIG. 6, the design pattern data used in the formation of a pattern of the sample 1 is stored in the magnetic disk device 109 as an example of a storage device (storage part).

The graphics included in the design pattern are based on a rectangular shape and a triangular shape. The magnetic disk device 109 stores the graphic data which is information including coordinates of a reference position of a graphic, a length of a side, and a figure code which is an identifier used for discriminating kinds of graphics such as a rectangular shape and a triangular shape and defines, for example, the shape, size, and position of each pattern graphic.

A set of graphics existing within a range of approximately several ten μm is generally referred to as a cluster or a cell, and data is hierarchized using the cluster or the cell. In the cluster or the cell, arrangement coordinates and repetition description in a case where various kinds of graphics are singly arranged or repeatedly arranged at certain intervals are defined. The cluster or cell data is disposed in a frame. The frame is, for example, a strip-shaped region having a width of several hundred μm and a length of approximately 100 mm corresponding to the entire length in the X or Y direction of the sample 1.

<Pattern Generation Process>

S3 of FIG. 8 is the pattern generation process. In this process, the pattern generation circuit 111 of FIG. 6 reads out the design pattern data from the magnetic disk device 109 via the control calculator 110 and converts the read-out design pattern data of the sample 1 into binary or multivalued image data (design image data). The image data is sent to the reference circuit 112.

When the design pattern data which becomes the graphic data is input to the pattern generation circuit 111, the pattern generation circuit 111 develops the design pattern data into data for each graphic and interprets a graphic code showing a graphic shape of the graphic data, a graphic size, and so on. The pattern generation circuit 111 then develops the binary or multivalued design image data as a pattern arranged in a square using, as units, grids with a predetermined quantization size. In the developed design image data, the occupancy of graphics in the design pattern for each region (square) corresponding to a sensor pixel is calculated. The graphic occupancy in each pixel becomes a pixel value.

<Filtering Process>

S4 of FIG. 8 is the filtering process. In this process, the reference circuit 112 of FIG. 6 applies a suitable filter to the design image data which is the image data of a graphic sent to the reference circuit 112.

Figure 9:
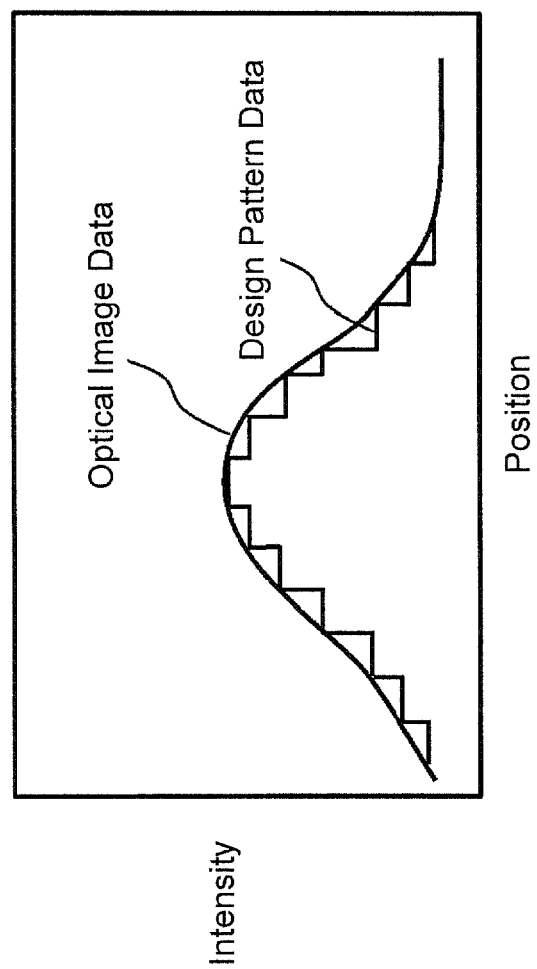
FIG. 9 is a view for explaining the filtering process.

FIG. 9 is a view for explaining the filtering process.

The measurement data as an optical image obtained from the sensor circuit 106 of FIG. 6 is in a state in which a filter is operated by, for example, the resolution characteristics of the lens 104 and the aperture effects of the photodiode array 105, and, in other words, in an analogue state in which the filter is continuously changed. Accordingly, the filtering process is applied to the design pattern data which is the image data on the design side, in which image intensity (gray value) is a digital value, whereby the design pattern data can be suited to the measurement data. Thus, the reference image to be compared with the optical image is created.

<Comparison Process>

S5 of FIG. 8 is the comparison process. In FIG. 6, the optical image data from the sensor circuit 106 is sent to the comparison circuit 108. The design pattern data is converted into the reference image data by the pattern generation circuit 111 and the reference circuit 112 and sent to the comparison circuit 108.

In the comparison circuit 108, the optical image sent from the sensor circuit 106 and the reference image generated in the reference circuit 112 are compared with each other using an appropriate comparative determination algorithm. When an error exceeds a predetermined value, the corresponding portion is determined as a defect. Subsequently, the coordinates of the defect and the optical image and the reference image as a basis for the defect determination as inspection results 205 illustrated in FIG. 7 are stored in the magnetic disk device 109.

The defect determination can be performed by the following two kinds of method. In one of the methods, when a difference exceeding a predetermined threshold size is admitted between a position of a contour line in the reference image and a position of a contour line in the optical image, it is determined that there is a defect. In the other method, when a ratio of a line width of a pattern in the reference image to a line width of a pattern in the optical image exceeds a predetermined threshold value, it is determined that there is a defect. In this method, a ratio of a distance between patterns in the reference image to a distance between patterns in the optical image may be used.

The inspection result 205 obtained as mentioned above is sent to a review apparatus 500, as illustrated in FIG. 7. The review is an operation for judging whether a detected defect becomes a practical problem. More specifically, the inspection result 205 is sent to the review apparatus 500, and it is judged whether the optical image should be modified by the operator. At this time, the operator performs the review while visually comparing the reference image as a basis of the defect determination with the optical image including a defect.

In the review apparatus 500, an image of a defect portion of the sample 1 is displayed while the table on which the sample 1 is placed is moved so that each coordinate of defects can be observed. At the same time, the images are arranged and displayed on a screen of a calculator of the review apparatus 500 so that the optical image and the reference image as the judgment conditions of the defect determination and the basis of the defect determination can be confirmed.

When the inspection apparatus 100 is equipped with the review apparatus 500, the image of the defect portion of the sample 1 is displayed using an observation optical system of the inspection apparatus 100. At the same time, the optical image and the reference image as the determination conditions of the defect determination and the basis of the defect determination are displayed using the screen of the control calculator 110 illustrated in FIG. 6.

The defect information discriminated through the review process is stored in the magnetic disk device 109 of FIG. 6. In FIG. 7, when at least one defect to be modified is confirmed in the review apparatus 500, the sample 1 is sent to a modification apparatus 600 as an exterior apparatus of the inspection apparatus 100. Since a modification method is different depending on whether the type of the defect is a protrusion-type defect or a recess-type defect, the types of the defect including the distinction between the protrusion type and the recess type and the coordinates of the defect are attached to a defect information list 207.

Embodiment 2

Figure 10:
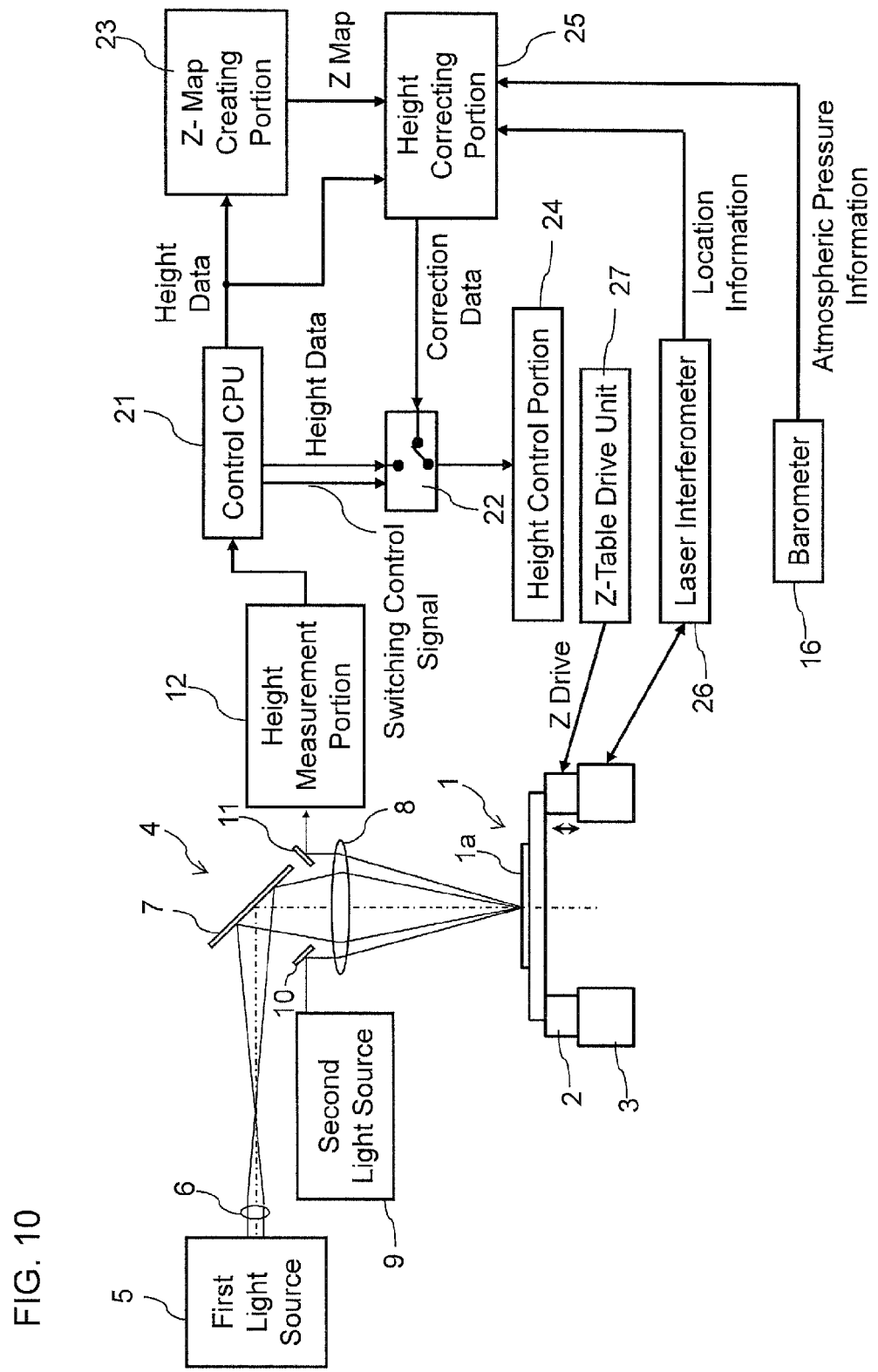
FIG. 10 is a diagram illustrating the configuration of an automatic focus mechanism according to embodiment 2.

FIG. 10 is a diagram illustrating the configuration of an automatic focus mechanism according to the present embodiment. The autofocus device is suitable for inspection of a sample having a step portion on a surface to be inspected, for example, inspection of a template used in the nanoimprint lithography.

In FIG. 10, a sample 1 is mounted on a Z table 2 provided to be movable in the vertical direction. The table 2 is movable in the horizontal direction by a XY table 3. The sample 1 has a mesa structure in which the central portion protrudes relative to the outer circumferential portion, and a pattern is formed on a rectangular mesa portion 1a.

An optical system 4 is disposed above the sample 1. In the optical system 4, a first light source 5 applies light for defect inspection to the sample 1. The light emitted from the first light source 5 is transmitted through a lens 6 to change the direction by a mirror 7, and, thus, to be converged on the sample 1 by a lens 8. A photodiode array (not illustrated) is disposed under the sample 1, and light transmitted through the sample 1 is imaged on the photodiode array, so that an optical image to be described later is generated.

In the optical system 4, a second light source 9 applies light for height measurement to the sample 1. The direction of the light emitted from the second light source 9 is changed via the mirror 10, and the light is irradiated onto the sample 1. Subsequently, the light is reflected from the sample 1 and then enters a height measuring portion 12 via the mirror 11. In FIG. 10, a light projecting lens through which the light emitted from the second light source 9 is focused on the sample 1 and a light receiving lens which receives the light reflected from the sample 1 and converges the light are omitted.

The height measuring portion 12 has a light-receiving element (not illustrated). As the light-receiving element, a position sensitive detector (PSD) is used, for example.

In the height measuring portion 12, a signal output from the light-receiving element is converted from a current value to a voltage value by an I/V conversion amplifier. After that, the signal is amplified to a suitable voltage level by a noninverting amplification amplifier and then converted into digital data in an A/D converting portion, and the height data of the surface of the sample 1 corresponding to a position of light detected by the light-receiving element is created.

The height data created in the height measuring portion 12 is sent to a control CPU (Central Processing Unit) 21. The control CPU 21 is a signal generating portion according to this invention and generates different signals according to whether an inspection target has a mesa portion. The signal is sent as a switch control signal to a signal switching portion 22. In this embodiment, since the sample 1 has the mesa portion 1a, the switch control signal is sent from the control CPU 21 to the signal switching portion 22 so that the height data is sent from the control CPU 21 to the Z map creating portion 23. On the other hand, when a sample having no mesa portion is inspected, the switch control signal is sent from the control CPU 21 to the signal switching portion 22 so that the height data is sent from the control CPU 21 to a height control portion 24.

When the height data is sent from the control CPU 21 to the Z map creating portion 23, a Z map (height map) is created based on the height data in the Z map creating portion 23.

Figure 11:
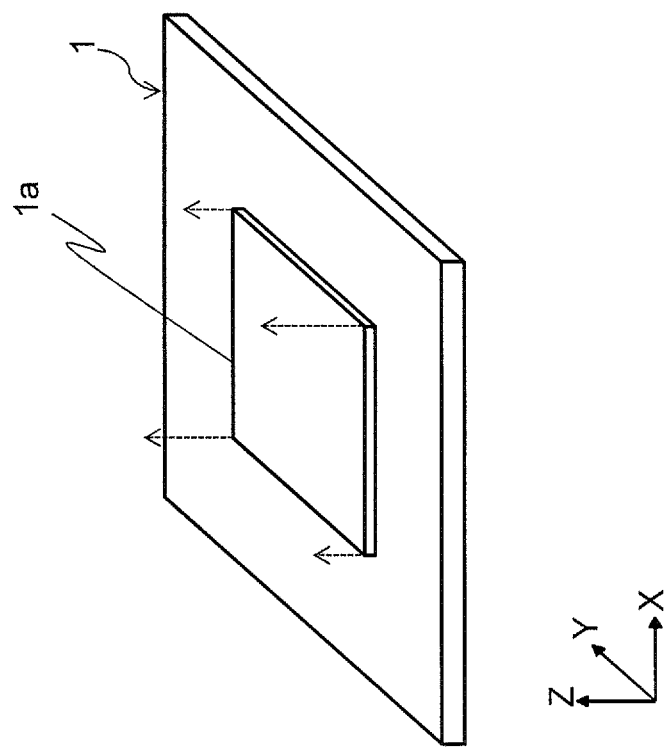
FIG. 11 is a schematic diagram of the sample according to the embodiment 2.

FIG. 11 is a schematic diagram of the sample 1. The four arrows at the four corners of the mesa portion 1a represent height measurement positions, and a difference between the lengths of the respective arrows represent the difference between the height data at the respective measurement positions. The height measurement position is not limited to the four corners as long as it is a corner position, and the number of measurement is not limited to four points.

Figure 12:
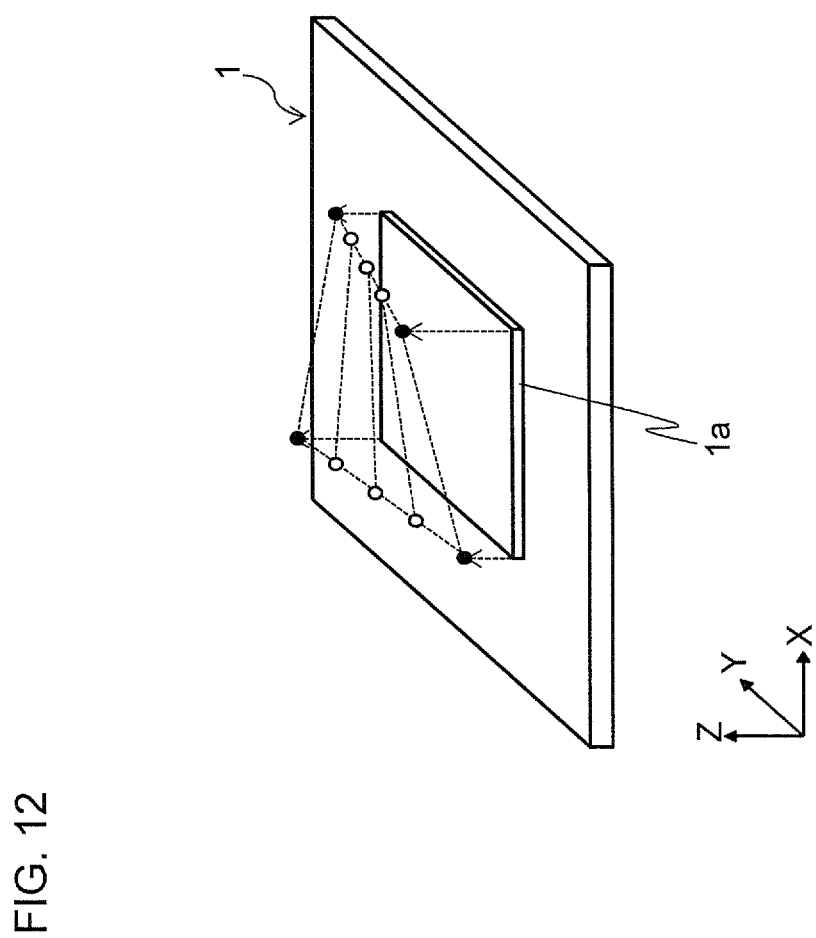
FIG. 12 is a diagram illustrating a height map of a sample of FIG. 11.

In the Z map creating portion 23 of FIG. 10, the height data of the four corners of the mesa portion 1a created in the height measuring portion 12 is linearly interpolated to create the Z map. The black circles of FIG. 12 show the height data measured in the height measuring portion 12. The white circles of FIG. 12 show the height data obtained by linear interpolation based on measured values. The dotted line connecting the height data measured at the four corners and the height data obtained by linear interpolation is the Z map.

In FIG. 10, the data of the Z map created in the Z map creating portion 23 is sent to a height correcting portion 25. Further, the height data from the control CPU 21 is sent to the height correcting portion 25. Furthermore, the atmospheric pressure information from a barometer 16 and positional information of the XY table 3 measured by a laser interferometer 26 are sent to the height correcting portion 25.

Figure 13:
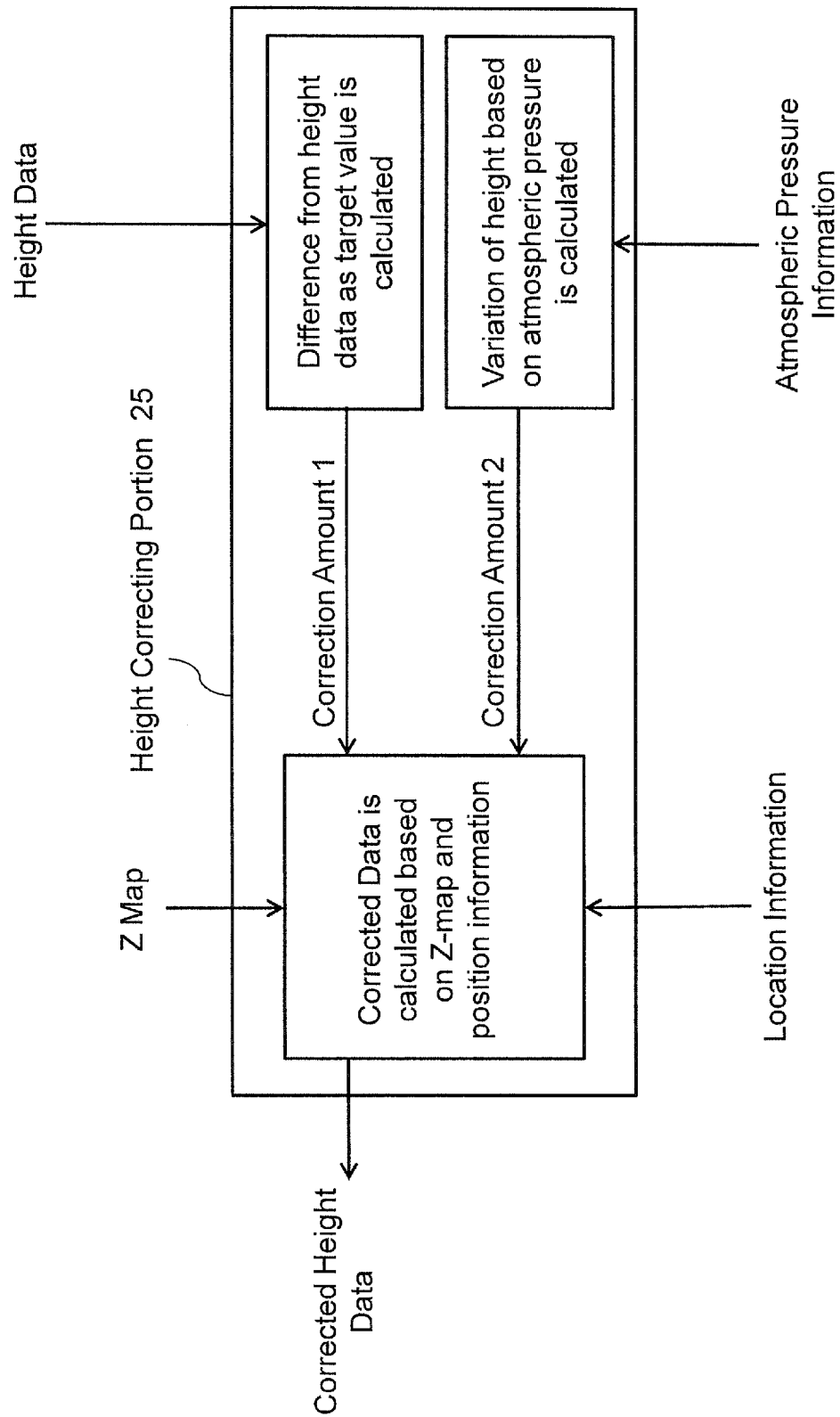
FIG. 13 is a view illustrating a flow of data in the height correcting portion of FIG. 10.

FIG. 13 is a view illustrating a flow of data in the height correcting portion 25. The data of the Z map sent from the Z map creating portion 23 of FIG. 10 is input to the height correcting portion 25. The height correction is performed using the Z map, whereby the distance between the optical system 4 and the sample 1 can be fixed not only when the pattern surface of the mesa portion 1a is inclined in one direction relative to the horizontal surface but also when the pattern surface is twisted.

When the atmospheric pressure and temperature change in the inspection process, the focal position of light irradiated to the mesa portion 1a is changed over time, and each height data of the four corners of the mesa portion 1a fluctuates. Thus, the data of the Z map is required to be corrected according to the changes of the atmospheric pressure and temperature. In this embodiment, the data of the Z map is corrected by the height data from the control CPU 21 and the atmospheric pressure information from the barometer 16. More specifically, when the height data obtained for each inspection frame is input from the control CPU 21, a difference (correction amount 1) from a target value, for example, a height where the focal position of light irradiated to the mesa portion 1a coincides with the pattern surface is calculated. When the atmospheric pressure information is input from the barometer 16, the variation (correction amount 2) according to the atmospheric pressure at the focal position of light irradiated to the mesa portion 1a is obtained. More specifically, the correction amount 2 is obtained from the atmospheric pressure measured by the barometer 16 based on a relationship between the atmospheric pressure and the focus displacement (as described in FIG. 4 in the embodiment 1).

The data of the Z map corresponding to the positional information of the XY table 3 measured by the laser interferometer 26 is corrected using the correction amount 1 and the correction amount 2 obtained as described above. The corrected height data is sent to the height control portion 24.

In FIG. 10, the height control portion 24 controls a Z table driving device 27 based on the corrected height data sent from the height correcting portion 25, whereby the inspection can be performed while the distance between the optical system 4 and the sample 1 can be kept constant. When a sample having no mesa portion is inspected, the height data is sent from the control CPU 21 to the height control portion 24, and the height control portion 24 controls the Z table driving device 27 based on the height data.

Although the inspection apparatus in this embodiment includes the automatic focus mechanism of FIG. 10, the constitution other than this is similar to that of the inspection apparatus 100 of FIG. 6 described in the embodiment 1.

Namely, an inspection apparatus according to the present invention, includes an optical image acquisition unit A and a control unit B, as in the inspection apparatus 100 shown in FIG. 6.

The optical image acquisition unit A has the first light source 5, the XY table 3 movable in the horizontal direction (X and Y directions), the lenses 6 and 8, the lens 104, the mirror 7, the photodiode array 105, the sensor circuit 106, the laser length measurement system 122, and the autoloader 130 as illustrated in FIG. 6. The XY table 3 has a structure capable of moving in a rotational direction (θ direction).

The operation of the control portion B is similar to that in the inspection apparatus 100 and will be described as follows using FIG. 6.

The control calculator 110 responsible for the overall control of the inspection apparatus 100 is connected to the position circuit 107, the comparison circuit 108, the reference circuit 112, the pattern generation circuit 111, the autoloader control circuit 113, the table control circuit 114, the magnetic disk device 109 as an example of a storage device, the magnetic tape device 115, the flexible disk device 116, the CRT (Cathode Ray Tube) 117, the pattern monitor 118, and the printer 119 via the bus 120 as a data transmission path. The XY table 3 is driven by the X-axis motor and the Y-axis motor controlled by the table control circuit 114. As those motors, a step motor may be used, for example.

Design pattern data, which is database reference data, is stored in the magnetic disk device 109 and read out in accordance with progression of the inspection to be sent to the pattern generation circuit 111. In the pattern generation circuit 111, the design pattern data is converted into image data (design pixel data). After that, the image data is sent to the reference circuit 112 and used in the generation of a reference image.

The inspection apparatus of the present embodiment may include other well-known components required for the inspection of the sample 1 in addition to the above-mentioned constituent elements. For example, the inspection apparatus itself may have a review device.

Figure 14:
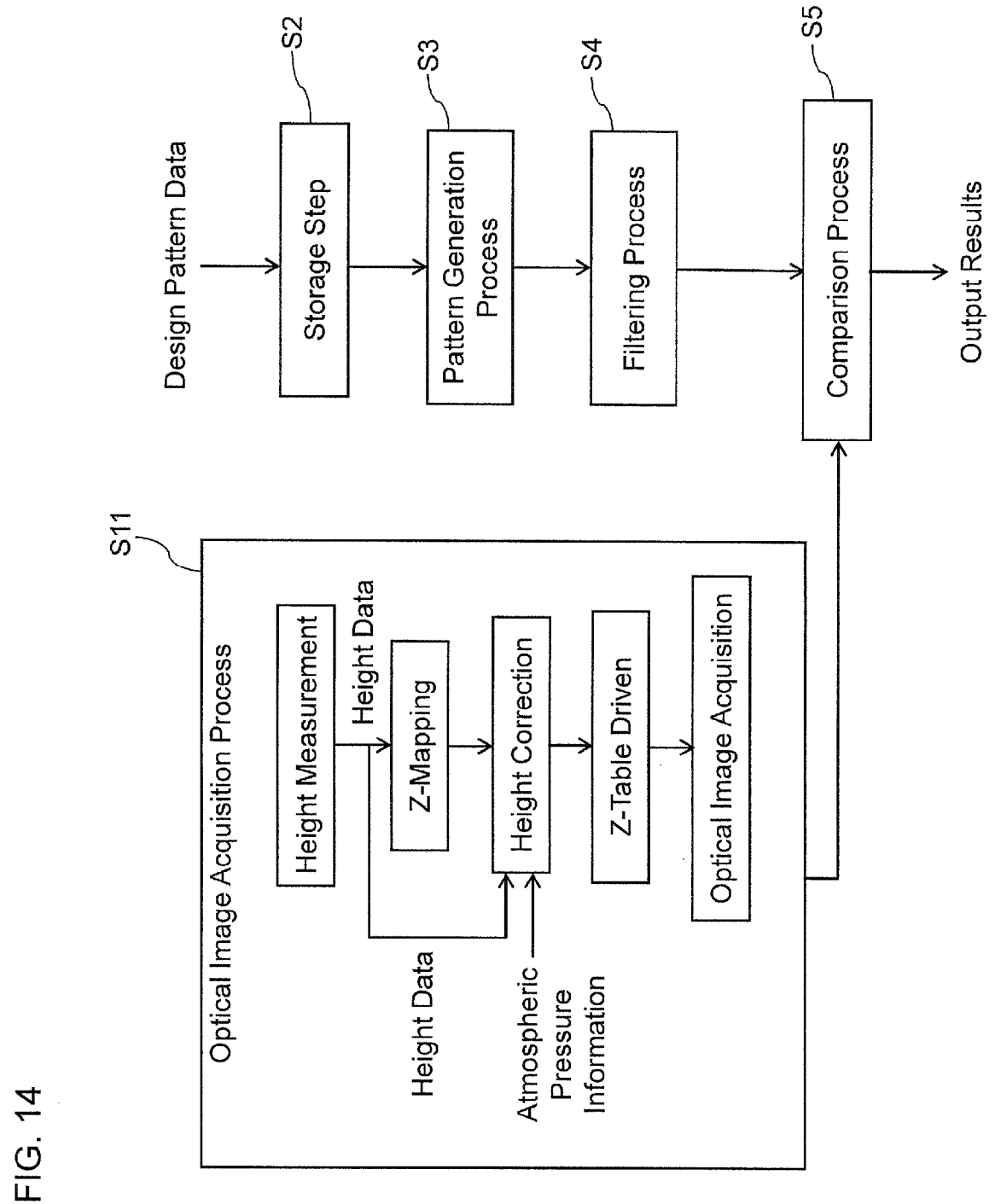
FIG. 14 is a flowchart showing an inspection process according to the embodiment 2.

FIG. 14 is a flowchart showing an inspection process according to the present embodiment. Hereinafter, an inspection method according to a die-to-database method will be described. Accordingly, a reference image compared with an optical image to be inspected is a reference image created based on drawing data (design pattern data). However, the inspection apparatus of the present invention can be applied to the inspection method according to the die-to-database method, and a reference image in this case is an optical image different from the optical image to be inspected.

As illustrated in FIG. 14, the inspection process has an optical image acquisition process (S11), a storage process (S2) for the design pattern data, a pattern generation process (S3) and a filtering process (S4) as examples of a reference image generation process, and a comparison process (S5) for an optical image and a reference image. Since the processes S2 to S5 are similar to those of FIG. 8 in the embodiment 1, and description thereof will be omitted.

In FIG. 14, in the optical image acquisition process S11, the optical image (measurement data) of the sample 1 is obtained. The optical image is an image of the sample 1 on which a graphic based on graphic data included in design pattern is drawn.

The way in which an optical image used for inspecting the defects is acquired will be described using FIG. 5.

As illustrated in FIG. 5, the inspection region of the mesa portion 1a is virtually divided into the strip-shaped inspection frames with a scan width W in the Y direction, and the operation of the XY table 3 of FIG. 1 is controlled so that the respective divided inspection frames $20_1$, $20_2$, $20_3$, $20_4$, etc. are continuously scanned, and an optical image is obtained while the XY table 3 moves in the X direction. Then, images with the scan width W illustrated in FIG. 5 are continuously input to the photodiode array. After an image in the first inspection frame $20_1$ is obtained, images with the scan width W are similarly continuously input while an image in the second inspection frame $20_2$ is moved in the opposite direction this time. When the image in the third inspection frame $20_3$ is obtained, the XY table 3 moves in a direction opposite to the direction in which the image in the second inspection frame $20_2$ is obtained, that is, in the direction in which the image in the first inspection frame $20_1$ has been obtained. The diagonal portion of FIG. 5 schematically represents a region in which an optical image has been obtained as described above.

In this embodiment, for each of the inspection frames $20_1$, $20_2$, $20_3$, $20_4$, etc., the height of the mesa portion 1a is measured while scanning the inspection frame; thereafter, the height is compared with the height data of the Z map corresponding to the inspection frame, and an amount of displacement (difference) from the height data of the Z map is obtained. When the displacement amount (difference) of the height of the mesa portion 1a in the inspection frame $20_1$ is not less than a predetermined value relative to the height data of the Z map, in the inspection of the next inspection frame $20_2$ the height data is corrected so that the displacement amount (difference) is zero in the height correcting portion 25. More specifically, the position of the Z table 2 is adjusted based on the corrected height data by the Z table drive device 15 so that the height of the mesa portion 1a is a target value, and thereafter, the next inspection frame $20_2$ is scanned.

Next, a specific example of a method of obtaining the optical image will be described using FIGS. 10 and 13.

As shown in FIG. 10, the sample 1 is placed on the Z table 2. The Z table 2 can be moved in a horizontal direction by the XY table 3. More specifically, the XY table 3 is driven by a table control circuit under the control of a control calculator and can be moved by a drive system which drives the XY table 3 in the X and Y directions as shown in FIG. 6. The position of the movement of the XY table 3 is measured by the laser length measurement system 26 and sent to the height correcting portion 25 and the position circuit 107.

The first light source 5 applies light for defect inspection to the sample 1. The light emitted from the first light source 5 is transmitted through the lens 6 to change the direction via the mirror 7, and, thus, to be converged on the sample 1 by the lens 8.

A distance between the lens 8 and the sample 1 is kept constant as follows.

In FIG. 10, the second light source 9 applies light for height measurement to the sample 1. The direction of the light emitted from the second light source 9 is changed via the mirror 10, and the light is irradiated onto the sample 1. Subsequently, the light is reflected from the sample 1 and then enters the height measuring portion 12 via the mirror 11.

In the height measuring portion 12, the height data of the surface of the sample 1 is created. The height data created in the height measuring portion 12 is sent to a control CPU (Central Processing Unit) 21. The control CPU 21 generates different signals according to whether an inspection target has a mesa portion. The signal is sent as a switch control signal to a signal switching portion 22. In the present embodiment, since the sample 1 has the mesa portion 1a, the switch control signal is sent from the control CPU 21 to the signal switching portion 22 so that the height data is sent from the control CPU 21 to the Z map creating portion 23. On the other hand, when a sample having no mesa portion is inspected, the switch control signal is sent from the control CPU 21 to the signal switching portion 22 so that the height data is sent from the control CPU 21 to a height control portion 24.

When the height data is sent from the control CPU 21 to the Z map creating portion 23, a Z map is created based on the height data in the Z map creating portion 23. The data of the Z map created in the Z map creating portion 23 is sent to a height correcting portion 25. Further, the height data from the control CPU 21 is sent to the height correcting portion 25. Furthermore, the atmospheric pressure information (that is, atmospheric pressure data such as measurement value of the atmospheric pressure) from a barometer 16 and positional information of the XY table 3 measured by a laser interferometer 26 are sent to the height correcting portion 25.

As illustrated in FIG. 13, when the height data is input from the control CPU 21, a difference (correction amount 1) from the height data as target data is calculated. When the atmospheric pressure information is input from the barometer 16, a variation (correction amount 2) of the height based on the atmospheric pressure is calculated. Further, the data of the Z map corresponding to the positional information of the XY table 3 measured by the laser interferometer 26 is corrected using the correction amount 1 and the correction amount 2 obtained as described above. The corrected height data is sent to the height control portion 24.

Next, the height control portion 24 controls a Z table driving device 27 based on the corrected height data sent from the height correcting portion 25, whereby the inspection can be performed while the distance between the optical system 4 and the sample 1 can be kept constant.

In FIG. 10, the light irradiated from the first light source 5 and transmitted through the sample 1 is imaged as an optical image on a photodiode array (not illustrated) disposed under the sample 1. A procedure of obtaining the optical image in the inspection region of the sample 1 is as described in the embodiment 1.

Namely, an image of a pattern imaged on the photodiode array is photoelectrically converted by the photodiode array and further A/D (analogue/digital) converted by the sensor circuit. An image sensor is disposed on the photodiode array. As the image sensor of the present embodiment, a line sensor in which CCD cameras as imaging devices are arranged in a row is used, for example. The line sensor includes a TDI (Time Delay Integration) sensor. In the present embodiment, for example, a pattern of the sample 1 is imaged by the TDI sensor while the XY table 3 of FIG. 10 continuously moves in the X-axis direction.

The optical image thus obtained in the optical image acquisition process (S11) is sent to the comparison circuit 108. The design pattern data of the sample 1 is converted into the reference image data by the pattern generation circuit and the reference circuit and sent to the comparison circuit.

In the comparison circuit, the optical image sent from the sensor circuit and the reference image generated in the reference circuit are compared with each other using an appropriate comparative determination algorithm. When an error exceeds a predetermined value, the corresponding portion is determined as a defect. Subsequently, the coordinates of the defect and the optical image and the reference image as a basis for the defect determination as inspection results are stored in the magnetic disk device.

The defect determination can be performed by the following two kinds of method. In one of the methods, when a difference exceeds a predetermined threshold size between a position of a contour line in the reference image and a position of a contour line in the optical image, it is determined that there is a defect. In the other method, when a ratio of a line width of a pattern in the reference image to a line width of a pattern in the optical image exceeds a predetermined threshold value, it is determined that there is a defect. In this method, a ratio of a distance between patterns in the reference image to a distance between patterns in the optical image may be used.

According to the present invention, as mentioned above, a sample having a mesa portion with a pattern can be accurately inspected.

The present invention is not limited to the embodiments described above and can be implemented in various modifications without departing from the spirit of the invention.

The above description of the present embodiment has not specified apparatus constructions, control methods, etc. which are not essential to the description of the invention, since any suitable apparatus constructions, control methods, etc. can be employed to implement the invention. Further, the scope of this invention encompasses all pattern inspection systems and pattern inspection methods employing the elements of the invention and variations thereof which can be designed by those skilled in the art.

What is claimed is:

1. An inspection method comprising:
placing a sample, which has a mesa portion having a pattern thereon, on a table;
irradiating light to the mesa portion through an optical system, and receiving light reflected by the mesa portion for measuring a height of the mesa portion;
creating a height map of the mesa portion based on a height of corner positions of the mesa portion;
correcting a height of the mesa portion using the height map based on an amount of difference between a height data of the height map of the mesa portion and a target value, and a temporal variation of a focal position of light irradiated to the mesa portion;
obtaining an optical image of the pattern while controlling a height of a position of the table based on the corrected height of the mesa portion; and
comparing the optical image with a reference image and determining a defect when a difference value between the optical image and the reference image is more than a predetermined threshold value.

2. The inspection method according to claim 1, wherein the height of the mesa portion is measured while the optical image of the pattern is obtained, and a temporal variation of the focal position of light is obtained based on the height of the measured mesa portion.

3. The inspection method according to claim 1, wherein a temporal variation of the focal position of light is obtained from a change of atmospheric pressure.

4. An inspection method comprising:
placing a sample, which has a mesa portion having a pattern thereon, on a table;
irradiating light to the mesa portion through an optical system, and receiving light reflected by the mesa portion for measuring a height of the mesa portion to obtain an inclination amount of a surface having the pattern relative to a horizontal surface of sample;
creating a height map of the mesa portion based on the height of the corner positions of the mesa portion;
correcting a height of the mesa portion using the height map based on an amount of difference between a height data of the height map of the mesa portion and a target value, and a temporal variation of a focal position of light irradiated to the mesa portion;
obtaining an optical image of the pattern while controlling a height of a position of the table based on the corrected height of the mesa portion; and
comparing the optical image with a reference image and determining a defect when a difference value between the optical image and the reference image is more than a predetermined threshold value,
wherein in the step of obtaining the optical image, when a measured value of the height of the mesa portion at one position is at a predetermined value or is more than a predetermined value, the measured value is corrected, the position of the table is adjusted based on the corrected measured value, and then the height of the mesa portion in the next frame is measured.

5. The inspection method according to claim 4, wherein the sample is supported at three points by supporting parts provided on the table, and in the step of inclining the sample, heights of the supporting parts at the three points are adjusted.

6. An inspection method comprising:
placing a sample, which has a mesa portion having a pattern thereon, on a table;
irradiating light to the mesa portion through an optical system, and receiving light reflected by the mesa portion for measuring a height of the mesa portion;
creating a height map of the mesa portion based on a height of corner positions of the mesa portion;
correcting the height of the mesa portion using the height map based on an amount of difference between a height data of the height map of the mesa portion and a target value, and a variation according to atmospheric pressure at the focal position of light irradiated to the mesa portion;
obtaining an optical image of the pattern while controlling a height of a position of the table based on the corrected height of the mesa portion; and
comparing the optical image with a reference image and determining a defect when a difference value between the optical image and the reference image is more than a predetermined threshold value.

7. An inspection apparatus comprising:
a table on which a sample is placed;
a light source which applies light toward the sample placed on the table;
a height measuring portion which receives the light from the light source reflected by the sample and creates height data of a surface of the sample;
a signal generating portion which generates different signals according to whether the sample has a mesa portion;
a signal switching portion which switches a destination to which the height data is transmitted according to a signal from the signal generation portion;
a map creating portion which receives the height data and creates a height map of the mesa portion based on a height of a corner positions of the mesa portion of the sample;
a height correcting portion which corrects the height of the mesa portion using the height map based on an amount of difference between a height data of the height map of the mesa portion and a target value, and a temporal variation of a focal position of light irradiated to the mesa portion;
a height control portion which receives the height data, or the corrected height data of the mesa portion corrected by the height correcting portion and controls a height of a position of the table;
an optical image acquisition portion which obtains an optical image of the sample; and
a comparison portion which compares the optical image with a reference image and determines a defect when a difference value between the optical image and the reference image is more than a predetermined threshold value.

8. The inspection apparatus according to claim 7, further comprising:
a barometer which measures atmospheric pressure,
wherein the height correcting portion receives the height data from the height measuring portion, the height map from the map creating portion, and the atmospheric pressure data measured by the barometer,
a difference between the height data from the height measuring portion and height data as a target value is a deviation from a target value of the measured value of the height of the mesa portion,
a variation of a height according to the atmospheric pressure obtained from the atmospheric pressure data is used as a temporal variation of the focal position of light irradiated to the mesa portion, and the height of the mesa portion obtained from the height map is corrected.

9. The inspection apparatus according to claim 7, wherein the sample is supported at three points by supporting parts provided on the table, and in the step of inclining the sample, heights of the supporting parts at the three points are adjusted.

* * * * *